US007082327B2

(12) United States Patent
Houben (10) Patent No.: US 7,082,327 B2
(45) Date of Patent: Jul. 25, 2006

(54) BIOMEDICAL SIGNAL ANALYSIS TECHNIQUES USING WAVELETS

(75) Inventor: Richard P. M. Houben, Lanaken (BE)

(73) Assignee: Medtronic, Inc., Minneapolis, MN (US)

( * ) Notice: Subject to any disclaimer, the term of this patent is extended or adjusted under 35 U.S.C. 154(b) by 466 days.

(21) Appl. No.: 10/414,758

(22) Filed: Apr. 16, 2003

(65) Prior Publication Data

US 2004/0210147 A1 Oct. 21, 2004

(51) Int. Cl.
*A61B 5/0402* (2006.01)

(52) U.S. Cl. ...................................... 600/509
(58) Field of Classification Search ............. None
See application file for complete search history.

(56) References Cited

U.S. PATENT DOCUMENTS

| | | | |
|---|---|---|---|
| 5,439,483 A | 8/1995 | Duong-Van | 607/5 |
| 5,730,142 A | 3/1998 | Sun et al. | |
| 5,755,739 A | 5/1998 | Sun et al. | |
| 5,778,881 A | 7/1998 | Sun et al. | |
| 5,782,888 A | 7/1998 | Sun et al. | |
| 6,324,421 B1 | 11/2001 | Stadler et al. | |
| 6,393,316 B1 | 5/2002 | Gillberg et al. | |
| 6,397,100 B1 | 5/2002 | Stadler et al. | |
| 6,438,419 B1 | 8/2002 | Callaway et al. | |
| 6,440,082 B1 | 8/2002 | Joo et al. | |

OTHER PUBLICATIONS

Bahoura, M. et al., "DSP Implementation of Wavelet Transform for Real Time ECG Wave forms Detection and Heart Rate Analysis," *Computer Methods and Programs in Biomedicine*, vol. 5, No. 52, p. 35-44 (1997).

Kohler, Bert-Uwe et al., "The Principles of Software QRS Detection," *IEEE Engineering in Medicine and Biology*, vol. 21, No. 1 p. 42-57 (Jan. 2002).

Koyrakh, L.A. et al., "Wavelet Transform Based Algorithms for EGM Morphology Discrimination for Implantable ICDs," *Computers in Cardiology*, vol. 26, p. 343-346 (Sep. 26, 1999).

Li, C. et al., "Detection of ECG Characteristic Points Using Wavelet Transforms," *IEEE*, vol. 42, No. 1, p. 21-28 (Jan. 1995).

Sahambi, J.S. et al., "Using Wavelet Transforms for ECG Characterization," *IEEE Engineering in Medicine and Biology*, vol. 16, No. 1, p. 77-83 (1997).

*Primary Examiner*—Scott M. Getzow
(74) *Attorney, Agent, or Firm*—Michael C. Soldner; Girma Wolde-Michael (57) ABSTRACT

The invention is directed to signal processing techniques for electrograms or other biomedical signals. In particular, the signal processing techniques make use of wavelet transformation of the electrograms. For example, an electrogram can be represented by a finite set of wavelets which comprise a decomposition of the electrogram in the scale-time domain. In accordance with the invention, wavelet analysis techniques can be used to distinguish specific phenomena in electrograms. For example, wavelet analysis can be used to distinguish between occurrences of large amplitude steep deflections, small amplitude steep deflections, and large amplitude shallow deflections of an electrogram.

30 Claims, 7 Drawing Sheets

BIOMEDICAL SIGNAL ANALYSIS TECHNIQUES USING WAVELETS

FIELD OF THE INVENTION

The invention relates to medical devices, and more particularly to signal processing of electrograms or other biomedical signals.

BACKGROUND OF THE INVENTION

A wide variety of medical devices have been developed in order to monitor patient conditions and possibly deliver therapy to the patient. In some cases, the medical devices comprise external medical devices that are used to monitor a patient. In other cases, the medical devices are implantable medical devices (IMDs) that are surgically implanted inside a patient for short or long term therapy. Telemetry can be used to communicate sensed information from one medical device to another medical device, e.g., from an IMD to an external medical device.

One common example of an IMD is a pacemaker. A pacemaker typically includes one or more pacing and sensing leads for delivery of pacing pulses to a patient's heart. Another example of an IMD is a combination pacemaker-cardioverter-defibrillator. Other examples include implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

Medical devices, including IMDs and external medical devices, often sense and record electrograms of a patient. Electrograms refer to signals which represent recorded changes in electric potential of the patient. Examples of electrograms include electrocardiograms, i.e., recorded electrical potentials associated with a patient's heart, and electroencephalograms, i.e., recorded electrical potentials associated with a patient's brain. Other more specific examples of electrograms include atrial electrograms, coronary sinus (CS) electrograms, esophageal electrograms, high right atrial (HRA) electrograms, His bundle electrograms, intraatrial electrograms, intracardiac electrograms, right ventricular electrograms, right ventricular apical electrograms, sinus node electrograms, and the like.

Signal processing of electrograms is a common challenge in the medical field. In particular, it is often necessary to identify specific features of an electrogram so that medical events can be identified in the patient, such as specific depolarizations in the patient's heart. For this reason, new and alternative techniques for processing electrograms are highly desirable. Signal processing of electrograms can be performed by any of a variety of medical devices including an IMD that senses the electrograms, an external medical device that senses the electrograms, or possibly an external medical device that receives sensed electrograms from another device, e.g., via telemetry.

BRIEF SUMMARY OF THE INVENTION

In general, the invention is directed to signal processing techniques for electrograms. In particular, the signal processing techniques make use of wavelet transformation of the electrograms. For example, an electrogram can be represented by a finite set of wavelets which comprise a decomposition of the electrogram in the scale-time domain. In accordance with the invention, wavelet analysis techniques can be used to distinguish specific phenomena in electrograms. For example, wavelet analysis can be used to distinguish between occurrences of large amplitude steep deflections, small amplitude steep deflections, and large amplitude shallow deflections of an electrogram. In this manner, wavelet analysis can be useful in identification of R waves, P waves and other electrogram events.

In one embodiment, the invention provides a method comprising converting an electrogram into a set of wavelets, the set of wavelets including wavelets at a fine scale and wavelets at a coarse scale, and identifying features of the electrogram based on whether the features appear in only the fine scale wavelets, only the coarse scale wavelets or both the fine and coarse scale wavelets.

In another embodiment, the invention provides a medical device comprising a wavelet transform unit to convert an electrogram into a set of wavelets, the set of wavelets including wavelets at a fine scale and wavelets at a coarse scale, and a wavelet analysis unit to identify features of the electrogram based on whether the features appear in only the fine scale wavelets, only the coarse scale wavelets or both the fine and coarse scale wavelets.

If implemented in software, the invention can be embodied in a computer readable medium comprising computer readable instructions that when executed convert an electrogram into a set of wavelets, the set of wavelets including wavelets at a fine scale and wavelets at a coarse scale, and identify features of the electrogram based on whether the features appear in only the fine scale wavelets, only the coarse scale wavelets or both the fine and coarse scale wavelets.

In another embodiment, the invention provides an apparatus comprising means for converting an electrogram into a set of wavelets, the set of wavelets including wavelets at a fine scale and wavelets at a coarse scale, and means for identifying features of the electrogram based on whether the features appear in only the fine scale wavelets, only the coarse scale wavelets or both the fine and coarse scale wavelets.

In another embodiment, the invention provides a method comprising converting an biomedical signal into a set of wavelets, the set of wavelets including wavelets at a fine scale and wavelets at a coarse scale, and identifying features of the biomedical signal based on whether the features appear in only the fine scale wavelets, only the coarse scale wavelets or both the fine and coarse scale wavelets.

The invention includes features that provide significant advances. For example, wavelet analysis can provide a relatively simple and straightforward mechanism for distinguishing among features or phenomena within electrograms. Accordingly, wavelet analysis can reduce the likelihood that the medical device will confuse the occurrence of large amplitude shallow deflections with the occurrence of large amplitude steep deflections. Similarly, implementation of the features of the present invention will enable the medical device to distinguish between the occurrence of large amplitude steep deflections and the occurrence of small amplitude steep deflections.

Moreover, the wavelet analysis techniques described herein can be well suited for implementation in IMDs, where computational resources are more limited and battery power is a concern. For example, the techniques described herein are much less computationally intensive than techniques in which correlation operations are performed to identify electrogram features.

The details of one or more embodiments of the invention are set forth in the accompanying drawings and the description below. Other features and aspects of the invention will be apparent from the description and drawings, and from the claims.

DETAILED DESCRIPTION OF THE INVENTION

The invention is directed to signal processing techniques for electrograms, or other biomedical signals, in which wavelet analysis is used. An electrogram can be represented by a finite set of wavelets which comprise a decomposition of the electrogram in the scale-time domain. In accordance with the invention, wavelet analysis techniques can be used to distinguish specific phenomena in electrograms or other biomedical signals. In particular, wavelet analysis can be used to distinguish between occurrences of large amplitude steep deflections, small amplitude steep deflections, and large amplitude shallow deflections of an electrogram. Although many details of the invention are described in the context of electrograms, the techniques are equally useful for analysis of other types of biomedical signals.

Large amplitude steep deflections in an electrogram correspond to large near field depolarizations, i.e., large depolarizations traveling in close proximity to a sensing electrode. In cardiac settings, identification of large amplitude steep deflections identify primary cardiac depolarizations at the given location. Small amplitude steep deflections correspond to small near field depolarizations, i.e., small depolarizations traveling in close proximity to the sensing electrode. In cardiac settings, identification of small amplitude steep deflections identify secondary cardiac depolarizations at the given location, e.g., commonly present during atrial fibrillation. Large amplitude shallow deflections in an electrogram correspond to primary far field depolarizations, i.e., large depolarizations not traveling in close proximity to the sensing electrode. In cardiac settings, identification of large amplitude shallow deflections identify a primary cardiac depolarization at a location that does not correspond to the sensing electrode, such as a ventricular depolarization sensed by an atrial electrode.

Distinguishing among large amplitude steep deflections, small amplitude steep deflections, and large amplitude shallow deflections of an electrogram can be challenging. However, wavelet analysis provides a relatively easy mechanism to do so. In particular, wavelets can be generated for an electrogram at various scales or scale factors. The scale factors span from a coarse scale to a fine scale. The coarse scale wavelets generally refer to wavelets having relatively large scale factors, whereas the fine scales generally refer to wavelets having relatively small scale factors. The terms coarse scale and fine scale, however, are generally relative and can assume different values in different embodiments.

Electrogram features that appear in all scales of wavelets can be identified as large amplitude steep deflections. Electrogram features that appear in fine scales but not coarse scales can be identified as small amplitude steep deflections. Electrogram features that appear in coarse scales but not fine scales can be identified as large amplitude shallow deflections. For example, the features can be said to appear in a given wavelet if a wavelet coefficient for that wavelet exceeds some predetermined threshold, and the threshold may be different for different scales.

In an electrogram, the differences between large amplitude steep deflections, small amplitude steep deflections, and large amplitude shallow deflections is generally relative, and can depend on the type of electrogram being analyzed. In other words, as used in this disclosure, the terms "large" and "small" are relative terms, and the terms "steep" and "shallow" are also relative terms. By way of example, amplitudes of atrial sensed atrial signals typically are in the range of 1–4 mV and have slopes exceeding 1 Volt per second. Atrial (unipolar) sensed ventricular signals are generally approximately 0.1–0.3 times the amplitude of atrial events, but this can vary considerably depending on the location of the atrial electrode, the indifferent electrode, and the size of the atrial electrode. The slope of atrial (unipolar) sensed ventricular signals is typically in the range of 0.1 Volts per second.

Despite the fact that the depolarization fields decrease with distance between the source and recording site, large far field depolarization wavefronts, e.g., ventricular depolarization recorded by an atrial electrode, can contribute significantly to recorded amplitudes of electrograms. The spatial sensitivity of recording electrodes is wide for distant sources contributing to the recorded signal. However, the bandwidth related to this distance phenomena is relatively low.

In normal homogeneously coupled atrial tissue, simultaneously recorded unipolar electrograms at various locations are typically biphasic with little morphological variation. Comparison of electrogram morphology recorded simultaneously from multiple neighboring locations can reveal information on local intercellular coupling either during atrial fibrillation or during normal sinus rhythm.

Spatial electrode sensitivity can be reduced by taking advantage of a priori information regarding the area of sensitivity related to recorded signal bandwidth. Wavelet transforms are particularly useful in analysis of non-stationary signals because wavelet transforms provide an alternative to the classical Short Time Fourier Transform (STFT) and Gabor transform. The wavelet transform is typically a linear operation that decomposes a signal into components that appear at different scales (or resolutions). A mother wavelet comprises a zero average function $\Psi \in L^2(R)$ (finite energy):

$$\int_{-\infty}^{\infty} \Psi(t)\,dt = 0 \quad \text{(Admissibility condition)} \qquad \text{EQUATION 1}$$

Equation 1 can be normalized $\|\Psi\|=1$, and centered round $t=0$. Then, a family of wavelets can be obtained by scaling and translation of the mother wavelet $\Psi$ by s, and translation by u:

$$\Psi_{u,s}(t) = \frac{1}{\sqrt{s}}\Psi\left(\frac{t-u}{s}\right) \quad \text{EQUATION 2}$$

Wavelet analysis allows the use of coarse wavelets where more precise low-frequency information is needed, and fine wavelets where high-frequency information is required. In analogy to the STFT, the wavelet transform is defined as the sum over all time of the signal multiplied by scaled, shifted versions of the wavelet function. For functions $f \in L^2(R)$ the wavelet transform at time u and scale s is defined as:

$$Wf(u,s) = <f, \Psi_{u,s}> = \int_{-\infty}^{\infty} f(t)\Psi^*\left(\frac{t-u}{s}\right)dt \quad \text{EQUATION 3}$$

This type of transform satisfies energy conservation. With decrease of scale 's', the support for the wavelet decreases and the wavelet becomes more sensitive to high-frequency components of the signal, enhancing finer grain details of the signal. An increase in scale, on the other hand, provides more emphasis on the coarse structure of the signal. The result of the wavelet transform can be defined in the scale-time plane. The wavelet transform can be rewritten as a convolution product:

$$Wf(u,s) = \int_{-\infty}^{\infty} f(t)\Psi^*\left(\frac{t-u}{s}\right)dt = f*\Psi_s(u), \quad \text{EQUATION 4}$$

where $$\Psi_s(t) = \frac{1}{\sqrt{s}}\Psi^*\left(\frac{-t}{s}\right) \quad \text{EQUATION 5}$$

The Fourier transform of $\Psi_s(t)$ is:

$$\hat{\Psi}(\omega) = \sqrt{s}\hat{\Psi}^*(s\omega) \quad \text{EQUATION 6}$$

It appears that $\hat{\Psi}$ is the transfer function of a band-pass filter, so the convolution can compute the wavelet transform with dilated impulse response band-pass filters.

Many electrograms, including electrocardiograms, carry most important information at their singularities and sharp deflections. The wavelet transform is particularly well adapted to characterize transient phenomena or singularities, because wavelet transforms decompose signals into building blocks well localized in time and frequency. The wavelet transform can focus on localized signal structures with a zooming procedure that progressively reduces the scale parameter 's.' A measure of local regularity of the signal is provided by the decay of the wavelet transform amplitude across its scales. Singularities can be detected by following the wavelet transform local maxima at fine scales.

$$|Wf(u,s)| \leq As^{\alpha+1/2} \quad \text{EQUATION 7}$$

From Equation 7, one can derive:

$$\log_2|Wf(u,s)| \leq \log_2 A + (\alpha+1/2)\log_2 s \quad \text{EQUATION 8}$$

Figure 1:
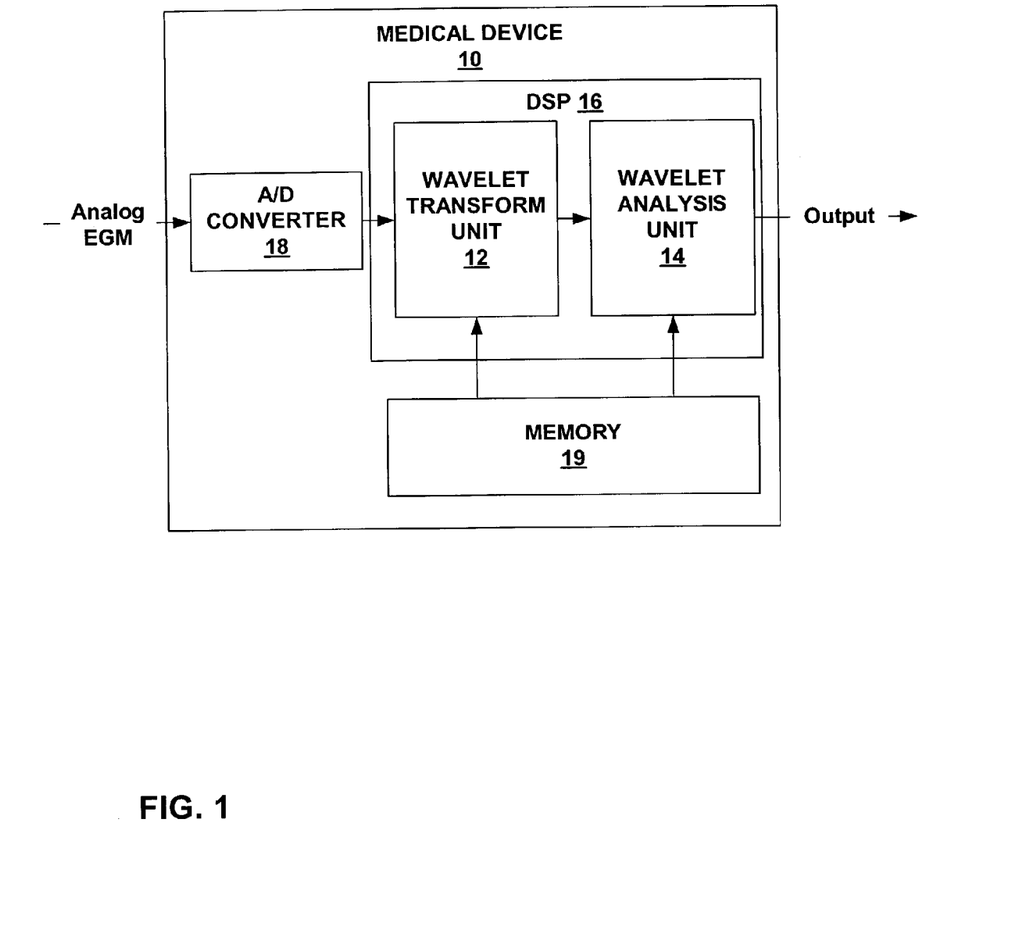
FIG. 1 is an exemplary block diagram of a medical device according to an embodiment of the invention.

FIG. 1 is an exemplary block diagram of a medical device 10 according to an embodiment of the invention. Medical device 10 may comprise any of a wide variety of medical devices used to analyze electrograms. For example, medical device 10 may comprise an implanted medical device (IMD) that includes various implanted electrodes (not shown) used for sensing the electrograms. Alternatively, medical device 10 may comprise an external medical device that uses surface electrodes on a patient's skin to sense the electrograms. Also, medical device can be an internal or external device that measure electrograms via subcutaneous electrodes. In other cases, medical device 10 may comprise an external device that receives sensed electrograms from another device, e.g., via telemetry. In any case, medical device 10 performs signal analysis on electrograms using wavelet analysis techniques as described herein.

In general, medical device 10 includes a wavelet transform unit 12 and a wavelet analysis unit 14. In the example illustrated in FIG. 1, wavelet transform unit 12 and a wavelet analysis unit 14 comprise software modules executed on a digital signal processor (DSP) 16. In that case, medical device 10 also includes memory 19 to store computer readable instructions that can be executed in DSP 16 to realize wavelet transform unit 12 and a wavelet analysis unit 14. For example, memory 19 can comprise random access memory (RAM), read-only memory (ROM), non-volatile random access memory (NVRAM), electrically erasable programmable read-only memory (EEPROM), flash memory, or the like.

Medical device 10 can also include an analog-to-digital (A/D) converter 18 to convert an analog electrogram to digital samples that comprise a digital electrogram. DSP 16 receives the digital electrogram and invokes wavelet transform unit 12 to transform the electrogram to wavelets and invokes wavelet analysis unit 14 to analyze the wavelets.

In other embodiments, however, wavelet transform unit 12 and a wavelet analysis unit 14 comprise dedicated hardware or logic that performs the functions described herein. Also, wavelet transform unit 12 and a wavelet analysis unit 14 can be implemented as one or more processors, application specific integrated circuits (ASICs), field programmable gate arrays (FPGAs), various combinations of hardware and software, or the like. Moreover, in some embodiments wavelet transform unit 12 and a wavelet analysis unit 14 can be implemented as analog logic circuits. In that case, the need for DSP 16 and A/D converter 18 could be eliminated. However, the illustrated example of FIG. 1, in which wavelet transform unit 12 and wavelet analysis unit 14 comprise software modules executed on DSP 16, are relatively easy and cost effective from an implementation standpoint. In that case, the software modules are initially stored in memory 19 and invoked by DSP 16 to execute the techniques described herein.

Medical device 10 receives an analog electrogram (EGM) and A/D converter 18 converts the analog electrogram to a digital electrogram, i.e., a stream of digital samples that represent the electrogram. Again, medical device receives the electrogram from one or more sensing electrodes of medical device 10, or receives the electrogram from another device used to sense the electrograms.

Wavelet transform unit 12 receives an electrogram (in this case in digital form), and performs wavelet transformation on the electrogram to generate a set of wavelets which collectively include the information in the electrogram. For example, wavelet transform unit 12 performs wavelet transformation using mathematical framework similar to that outlined above. In particular, the set of wavelets can be obtained by scaling and translation of a selected mother wavelet. Wavelet transform unit 12 can comprise a set of dilated impulse response band-pass filters designed to perform the desired wavelet transformation on the electrogram. The set of wavelets generated by wavelet transform unit 12 include numerous wavelets at various scale factors. The scale factors span from a coarse scale to a fine scale.

The coarse scale wavelets provide a larger overall picture of the electrogram, but lack specific details of the electrogram. The fine scale wavelets provide a less complete picture of the electrogram, but include more detail. The whole set of wavelets include wavelets of a number of different scale factors. The scale factors associated with coarse scale wavelets can be greater than or equal to 10 multiplied by scale factors associated with wavelets in the fine scale, although the invention is not necessarily limited in that respect.

Wavelet analysis unit 14 analyzes the generated wavelets to identify features of the electrogram based on the wavelets. In accordance with the invention, wavelet analysis unit 14 can distinguish between different electrogram features based on whether the features appear on coarse wavelets, fine wavelets, or both coarse and fine wavelets. Wavelet analysis unit 14 outputs results based on this analysis. For example, the output of wavelet analysis unit 14 can comprise an indication of identified features and the timing of the identified features within the electrogram.

More specifically, wavelet analysis unit 14 identifies electrogram features comprising large amplitude steep deflections when the features appear in all scales of wavelets. Also, wavelet analysis unit 14 identifies electrogram features comprising small amplitude steep deflections when the features appear in fine scales but not coarse scales. Moreover, wavelet analysis unit 14 identifies electrogram features comprising large amplitude shallow deflections when the features appear in coarse scales but not fine scales. In this manner, wavelet analysis unit 14 analyzes the wavelets to identify characteristics of the electrogram.

Figure 2A:
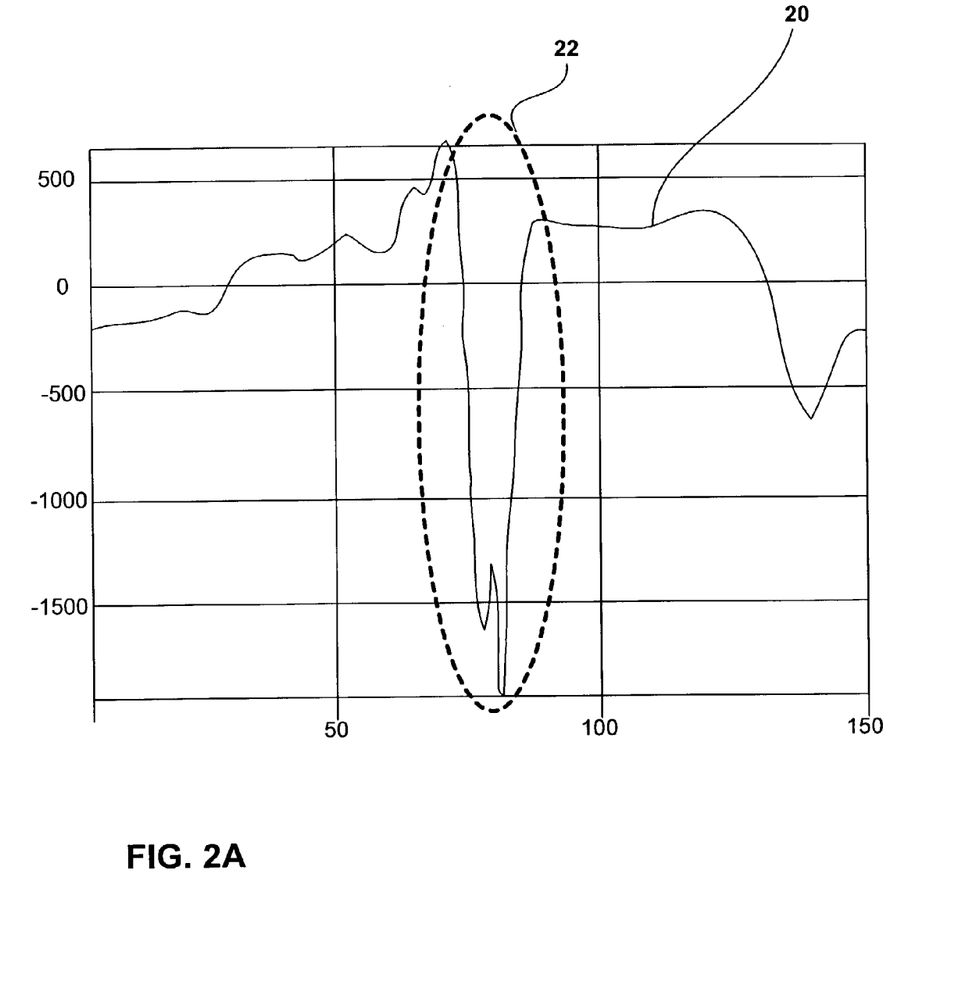
FIGS. 2A–2D are graphs of an exemplary electrogram comprising an atrial electrocardiogram.

FIG. 2A is a graph of an exemplary electrogram 20 comprising an atrial electrocardiogram, i.e., an electrogram of the heart sensed by an atrial electrode. The X-axis is in units of time (milliseconds) and the Y-axis is in units of amplitude (mV/200). Portion 22 is a large amplitude steep deflection in electrogram 20, and corresponds to large near field depolarization, i.e., a large depolarization traveling in close proximity to the sensing electrode. Thus, identification of the large amplitude steep deflection (portion 22) identifies primary cardiac depolarizations at the given location. Wavelet transform unit 14 identifies portion 22 as a large amplitude steep deflection because this electrogram feature appears in both coarse and fine wavelets.

Figure 2B:
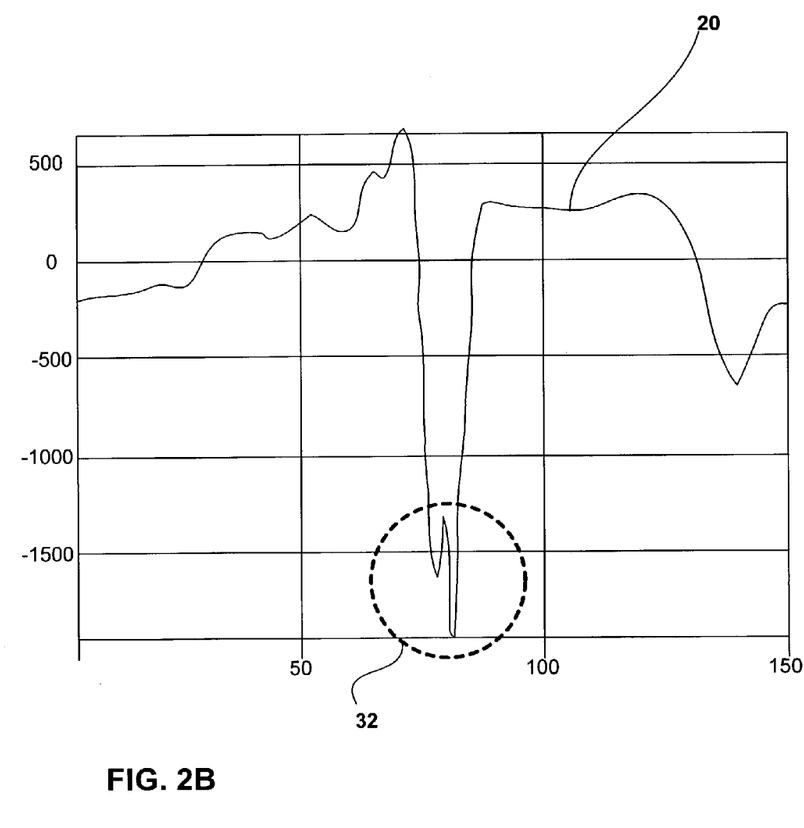

FIG. 2B is another graph of electrogram 20 comprising an atrial electrocardiogram. The X-axis is in units of time (milliseconds) and the Y-axis is in units of amplitude (mV/200). As illustrated in FIG. 2B, portion 32 is a small amplitude steep deflection in electrogram 20, and corresponds to a small near field depolarization, i.e., small depolarizations traveling in close proximity to the sensing electrode. Identification of small amplitude steep deflections (portion 32) identifies secondary cardiac depolarizations at the given location, e.g., commonly present during atrial fibrillation. Wavelet transform unit 14 identifies portion 32 as a small amplitude steep deflection because this electrogram feature appears in fine wavelets but does not appear in coarse wavelets.

Figure 2C:
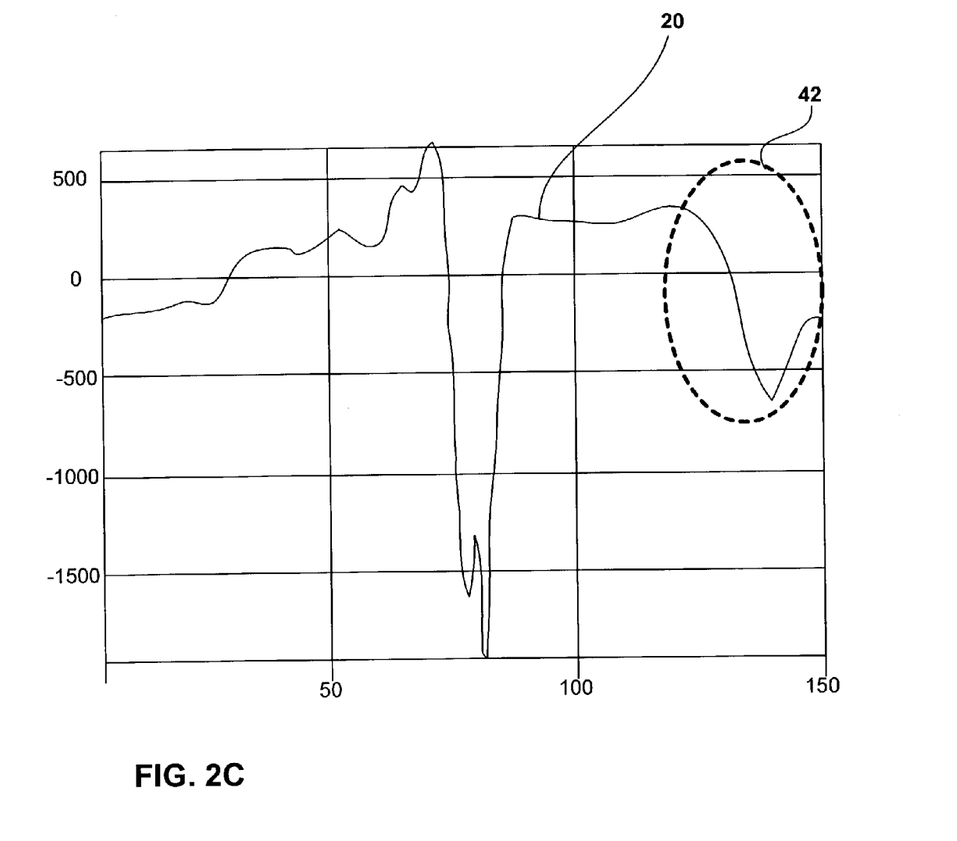

FIG. 2C is another graph of electrogram 20 comprising an atrial electrocardiogram. The X-axis is in units of time (milliseconds) and the Y-axis is in units of amplitude (mV/200). As illustrated in FIG. 2C, portion 42 is a large amplitude shallow deflection in electrogram 20, and corresponds to a primary far field depolarization, i.e., a large depolarization not traveling in close proximity to the sensing electrode. Identification of large amplitude shallow deflections (portion 42) identifies primary cardiac depolarizations at a location that does not correspond to the sensing electrode. Wavelet transform unit 14 identifies portion 42 as a large amplitude shallow deflection because this electrogram feature appears in coarse wavelets but does not appear in fine wavelets.

Such wavelet analysis provides a relatively simple and straightforward mechanism for distinguishing among features or phenomena within electrograms. Accordingly, medical device 10 is less likely to confuse the occurrence of large amplitude shallow deflections with the occurrence of large amplitude steep deflections. Similarly, medical device 10 is less likely to confuse the occurrence of large amplitude steep deflections with the occurrence of small amplitude steep deflections, and so forth. In this manner, signal processing of electrograms can be improved and simplified. In particular, the wavelet analysis techniques described herein are well suited for implementation in IMDs, where computational resources are more limited and battery power is a concern. For example, the techniques described herein are much less computationally intensive than techniques in which correlation operations are performed to identify electrogram features.

Figure 2D:
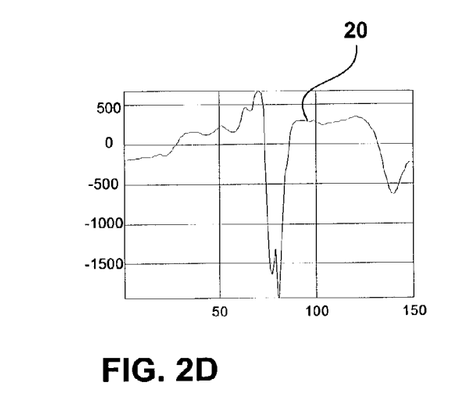

FIG. 2D is another graph of electrogram 20 comprising an atrial electrocardiogram. FIGS. 3–6 respectively illustrate traces of information contained in the wavelets of four different scales. In each of FIGS. 3–6, the X-axis is in units of time (milliseconds) and the Y-axis is in units of amplitude (mV/200).

Figure 3:
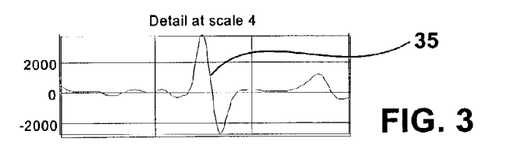
FIGS. 3–6 respectively illustrate traces of information contained in the wavelets of four different scales in relation to the electrogram illustrated in FIGS. 2A–2D.
Figure 4:
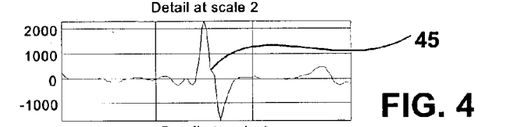
Figure 5:
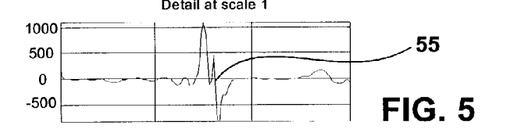
Figure 6:
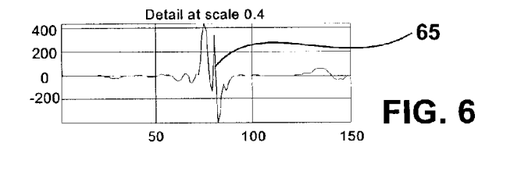

In particular, FIG. 3 illustrates a trace 35 associated with a scale factor of 4, FIG. 4 illustrates a trace 45 associated with a scale factor of 2, FIG. 5 illustrates a trace 55 associated with a scale factor of 1 and FIG. 6 illustrates a trace 65 associated with a scale factor of 0.4. The wavelets associated with trace 35 are fewer than the wavelets of the other traces because trace 35 represent the coarse wavelets in this example. In other words, every wavelet used to define trace 35 spans a larger portion of electrogram 20 than wavelets of the other traces 45, 55, 65.

On the other hand, the wavelets associated with trace 65 are more numerous than the wavelets of the other traces because trace 65 represents the fine wavelets in this example. In other words, every wavelet used to define trace 65 spans a smaller portion of electrogram 20 than wavelets of the other traces 35, 45, 55. Each respective trace 35, 45, 55, 65 is a general representation of the information collectively contained in all of the wavelets at the respective scale.

As can be appreciated by examining FIGS. 3–6, portion 22 (FIG. 2A) of electrogram 20 is identifiable in every trace 35, 45, 55, 65. In other words, the wavelets at every scale include information indicative of the large amplitude steep deflection associated with portion 22. Portion 32 (FIG. 2B) of electrogram 20, however, is identifiable only in traces 55, 65 and is generally not present in traces 35, 45. In other words, only the wavelets at fine scales include information indicative of the small amplitude steep deflection associated with portion 32.

Portion 42 (FIG. 2B) of electrogram 20, is identifiable only in traces 35, 45 and 55, but is difficult to identify in trace 65. At even finer scales, portion 42 would become completely unidentifiable. Thus, only the wavelets at more coarse scales include information indicative of the large amplitude shallow deflection associated with portion 42.

Wavelet analysis unit 14 exploits the fact that some features are identifiable in all scales, some features are identifiable only in coarse scales, and some features are identifiable only in fine scales. In particular, wavelet analysis unit 14 identifies large amplitude steep deflections when the features appear in all scales of wavelets, identifies small amplitude steep deflections when the features appear in fine scales but not coarse scales, and identifies large amplitude shallow deflections when the features appear in coarse scales but not fine scales. As used in this disclosure, the term "appear" generally means that the given feature can be identified in the respective scale. For example, if a given wavelet coefficient exceeds a particular predefined value, the feature can be identified and can be said to appear in the wavelet. Different predefined values can be used at different scales to determine whether a feature appears in a given wavelet, e.g., by comparing the give predefined value to the given wavelet coefficient. Other techniques, however, can also be used to determine whether a feature appears in a given wavelet.

Figure 7:
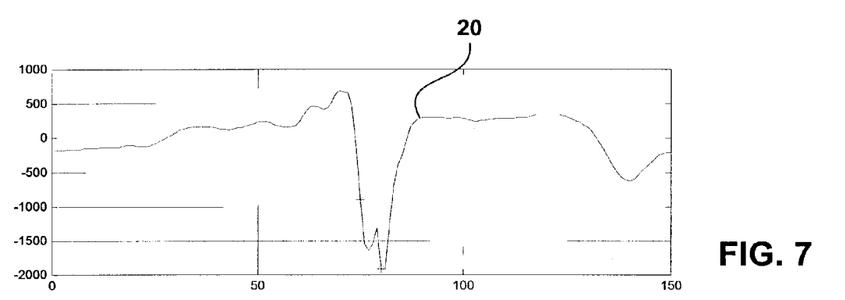
FIG. 7 is another graph of an exemplary electrogram comprising an atrial electrocardiogram.
Figure 8:
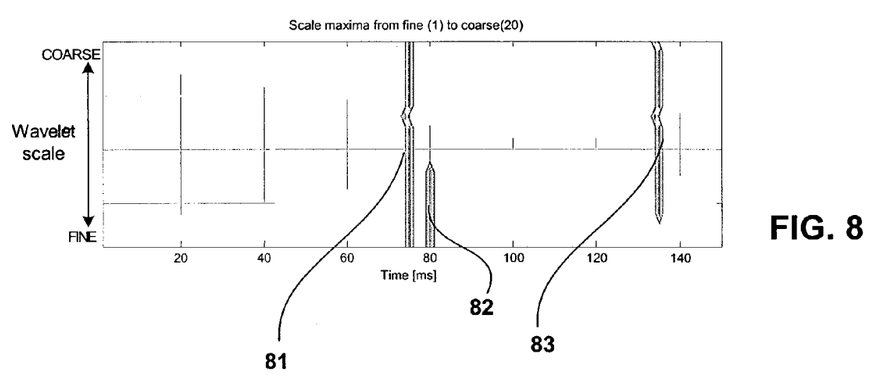
FIG. 8 is a graph illustrating scale maxima lines of various features of the electrogram of FIG. 7 across various scales from coarse to fine.

FIG. 7 is another graph of electrogram 20 comprising an atrial electrocardiogram. In FIG. 7, the X-axis is in units of time (milliseconds) and the Y-axis is in units of amplitude (mV/200). FIG. 8 is a corresponding graph illustrating scale maxima lines 81, 82, 83 of identifying features of electrogram 20 across various scales from coarse to fine. In FIG. 8, the X-axis is in units of time (milliseconds) and the Y-axis represents different scales of wavelets from coarse to fine.

The scale maxima lines 81, 82, 83 respectively identify whether the corresponding feature at that given time instance is identifiable in the wavelets at the different scales. As can be appreciated in FIG. 8, scale maxima line 81 spans all scales from coarse to fine. Thus, the feature associated with scale maxima line 81 is identifiable in wavelets of every scale from coarse to fine. Scale maxima line 81 corresponds to portion 22 (FIG. 2A) of electrogram 20. Thus, the large amplitude steep deflection associated with portion 22 appears in all scales of wavelets from coarse to fine.

Scale maxima line 82, on the other hand, is present only in fine scales. In particular, scale maxima line 82 stops as it approaches coarser scales. Thus, the feature associated with scale maxima line 82 is identifiable only in fine scale wavelets and not in coarse scale wavelets. Scale maxima line 82 corresponds to portion 32 (FIG. 2B) of electrogram 20. Thus, the small amplitude steep deflection associated with portion 32 appear only in fine scale wavelets.

Scale maxima line 83 is present only in the more coarse scales. In particular, scale maxima line 83 stops as it approaches the finest scales. Thus, the feature associated with scale maxima line 83 is identifiable in coarse scale wavelets and is not identifiable in the fine scale wavelets. Scale maxima line 83 corresponds to portion 42 (FIG. 2C) of electrogram 20. Thus, the large amplitude shallow deflection associated with portion 42 appears in coarse scale wavelets, but not fine scale wavelets. In accordance with the invention, wavelet analysis unit 14 exploits the phenomenon that some features are identifiable in all scales of wavelets, some features are identifiable only in coarse scales, and some features are identifiable only in fine scales.

Figure 9:
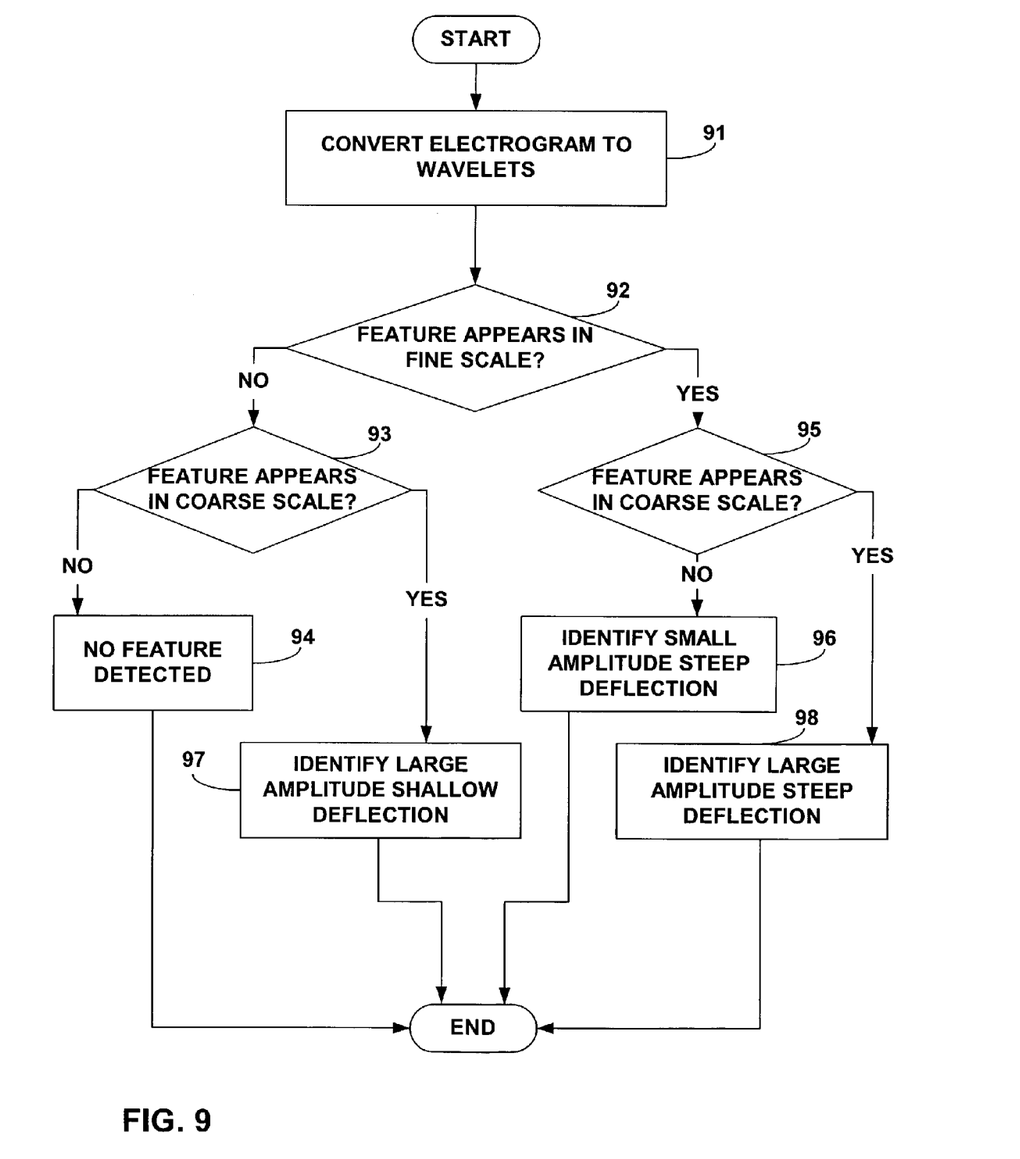
FIG. 9 is a flow diagram according to an embodiment of the invention.

FIG. 9 is a flow diagram according to an embodiment of the invention. As shown in FIG. 9, wavelet transform unit 12 performs wavelet transformation to convert an electrogram into wavelets (91). In particular, the set of wavelets can be obtained by scaling and translation of a selected mother wavelet as described above. The set of wavelets may include numerous wavelets at various scale factors. The scale factors span from a coarse scale to a fine scale.

Wavelet analysis unit 14 analyzes the generated wavelets to identify features of the electrogram based on the wavelets. In particular, wavelet analysis unit 14 determines whether features appear in various wavelets, e.g., by determining whether a given wavelet coefficient exceeds a particular value. If nothing appears in fine scale wavelets (no branch of 92) or coarse scale wavelets (no branch of 93), wavelet analysis unit 14 determines that no feature was detected (94). If an electrogram feature appears in fine scale wavelets (yes branch of 92), but do not appear in coarse scale wavelets (no branch of 95), wavelet analysis unit 14 identifies the feature as a small amplitude steep deflection (96). If an electrogram feature does not appear in fine scale wavelets (no branch of 92), but does appear in coarse scale wavelets (yes branch of 93), wavelet analysis unit 14 identifies the feature as a large amplitude shallow deflection (97). If an electrogram feature appears in both fine scale wavelets (yes branch of 92) and coarse scale wavelets (yes branch of 95), wavelet analysis unit 14 identifies the feature as a large amplitude steep deflection (98). In this manner, wavelet analysis unit 14 exploits wavelet analysis to identify electrogram features.

EXAMPLE

The wavelet transform techniques described herein were applied to a set of atrial signals obtained during acute atrial fibrillation. A database of electrograms contained each of the signals detected and extracted from the various electrodes positioned at various locations on the atrial free wall. All signals were annotated for their number of deflections originating from different simultaneous activation wavefronts. A range of one to five simultaneous wavefronts were used in the test. The test range was divided into two sub-sets with respect to the level of fragmentation. The first subset contained all single and double wavefronts while the second subset contained all triple, quad and penta wavefronts. All signals in the second subset were extracted from an acute atrial fibrillation database, and an equal size random sample of signals of the first subset was taken.

Some preprocessing steps were performed on the electrograms including wavelet denoising, e.g., by transforming the electrograms to wavelets, setting low amplitude wavelet coefficients to zero, and transforming the wavelets to generate denoised electrograms. The test set contained a total of 492 signals. No information regarding spatial relation was included in the test set of signals. The continuous wavelet transform was calculated for all the signals in the test set using the first derivative of a Gaussian function. This wavelet family was built starting from the Gaussian function, taking the first derivative of:

$$\Theta(t) = C_p e^{-t^2}, \qquad \text{EQUATION 9}$$

$$\text{where } \|\Theta^{(p)}\| = 1 \qquad \Psi(t) = \frac{d}{dt}\Theta(t) \qquad \text{EQUATION 10}$$

The wavelet transformation using the first derivative of the Gaussian function Θ, produced local maxima over the various scale pronounced down slopes of the electrogram signal.

A bandwidth assessment of the signals included in the test set revealed the analysis scales of the wavelet transform. Linear scales where fixed from normalized values of 1 to 20, with value 1 representing the finest scale and value 20 representing the coarsest scale. Next the maxima were identified starting from the finest scale towards the coarse scales. Local maxima where detected at the various scales using a threshold related to the signal standard deviation. In particular, the threshold was fixed to 0.5. Over the scales, chaining was achieved by allowing local maxima not to deviate not more 1 ms in both directions. Violation of this criterion stopped the chaining process. Several classes of wavefronts can be identified purely from time domain information.

Large amplitude steep deflections indicating massive activation wavefronts passing underneath the recording electrode allowed chaining throughout all available scales. Small amplitude steep deflections indicating one or more small wavefronts in the recording electrode vicinity exclusively produced maxima in the finest scales. Large amplitude shallow deflections indicating massive depolarization at a remote location exclusively produced maxima only in the coarse scales.

The following MATLAB pseudo-code, below, illustrates one exemplary implementation of the invention. In particular, the pseudo-code in Table 1 can be stored on a computer readable medium for execution in a DSP. In this manner, one embodiment of wavelet analysis unit 14 is realized in software executing on a DSP.

A number of embodiments of the invention have been described. However, one skilled in the art will appreciate that the invention can be practiced with embodiments other than those disclosed. For example, other types of mother wavelet functions can be used to generate the respective wavelets which are used in electrogram analysis. In addition, the invention can find application for analysis of a wide variety of different types of biomedical signals including but not limited to electrograms measured via external sensors, electrograms measured via implanted sensors, a signals measured by one or more a biomedical sensor, chronic or acute signals, or any other biomedical signal.

Also, although various techniques have been described as being implemented in software, similar techniques can be implemented in hardware, firmware, or the like. Example hardware implementations of wavelet transform unit 12 and wavelet analysis unit 14 include implementations within an application specific integrated circuit (ASIC), a field programmable gate array (FPGA), a programmable logic device, specifically designed hardware components, one or more processors, or any combination thereof. If implemented in software, a computer readable medium stores computer readable instructions, e.g., program code, that can be executed by a processor or DSP to carry out one or more of the techniques described above. For example, the computer readable medium can comprise random access memory (RAM), read-only memory (ROM), non-volatile random access memory (NVRAM), electrically erasable programmable read-only memory (EEPROM), flash memory, or the like. The computer readable medium can comprise computer readable instructions that when executed in a medical device carry out one or more of the techniques described herein. The disclosed embodiments are presented for purposes of illustration and not limitation, and the invention is limited only by the claims that follow.

What is claimed is:

1. An implantable medical device comprising:
a wavelet transform unit to convert an electrogram into a set of wavelets, the set of wavelets including wavelets at a fine scale and wavelets at a coarse scale; and
a wavelet analysis unit to identify features of the electrogram based on whether the features appear in only the fine scale wavelets, only the coarse scale wavelets or both the fine and coarse scale wavelets.

2. The implantable medical device of claim 1, wherein the electrogram comprises a digital electrogram, the medical device further comprising an analog-to-digital converter to convert an analog electrogram to the digital electrogram, wherein the wavelet transform unit converts the digital electrogram into the set of wavelet and the wavelet analysis unit distinguishes features of the digital electrogram.

3. The implantable medical device of claim 1, further comprising a digital signal processor, wherein the wavelet transform unit and the wavelet analysis unit comprise software modules executed by the digital signal processor.

4. The implantable medical device of claim 1, further comprising one or more electrodes to sense the electrogram.

5. The implantable medical device of claim 1, wherein the medical device comprises one of an external medical device and an implanted medical device.

6. The implantable medical device of claim 1, wherein the medical device receives the electrogram from another medical device via telemetry.

7. The implantable medical device of claim 1, wherein wavelets in the coarse scale have a scale factor greater than or equal to 10 multiplied by a scale factor associated with wavelets in the fine scale.

8. The implantable medical device of claim 1, wherein the wavelet analysis unit identifies a particular feature in the electrogram as a large amplitude steep deflection when the particular feature appears in the fine and coarse scale wavelets.

9. The implantable medical device of claim 1, wherein the wavelet analysis unit identifies a particular feature in the electrogram as a small amplitude steep deflection when the particular feature appears in the fine scales wavelets but not the coarse scale wavelets.

10. The implantable medical device of claim 1, wherein the wavelet analysis unit identifies a particular feature in the eleotrogram as a large amplitude shallow deflection when the particular feature appears in the coarse scale wavelets but not the fine scale wavelets.

11. The implantable medical device of claim 1, wherein the electrogram comprises an atrial electrocardiogram, wherein the wavelet analysis unit:
identifies a first feature in the atrial electrocardiogram as an indication of primary near field depolarization when the first feature appears in the fine and coarse scale wavelets;
identifies a second feature in the atrial electrocardiogram as a secondary near field depolarization when the second feature appears in the fine scales wavelets but not the coarse scale wavelets; and identifies a third feature in the atrial electrocardiogram as a far field primary depolarization when the third feature appears in the coarse scale wavelets but not the fine scale wavelets.

12. An implantable medical device comprising:
a wavelet transform unit to convert a biomedical signal into a set of wavelets, the set of wavelets including wavelets at a fine scale and wavelets at a coarse scale; and
a wavelet analysis unit to identity features of the biomedical signal based on whether the features appear in only the fine scale wavelets, only the coarse scale wavelets or both the fine and coarse scale wavelets.

13. A method comprising:
converting an electrogram into a set of wavelets, the set of wavelets including wavelets at a fine scale and wavelets at a coarse scale; and
identifying features of the electrogram based on whether the features appear in only the fine scale wavelets, only the coarse scale wavelets or both the fine and coarse scale wavelets.

14. The method of claim 13, wherein wavelets in the coarse scale have scale factors greater than or equal to 10 multiplied by a scale factor associated with wavelets in the fine scale.

15. The method of claim 13, further comprising identifying a particular feature in the electrogram as a large amplitude steep deflection when the particular feature appears in the fine and coarse scale wavelets.

16. The method of claim 13, further comprising identifying a particular feature in the electrogram as a small amplitude steep deflection when the particular feature appears in the fine scales wavelets but not the coarse scale wavelets.

17. The method of claim 13, further comprising identifying a particular feature in the electrogram as a large amplitude shallow deflection when the particular feature appears in the coarse scale wavelets but not the fine scale wavelets.

18. The method of claim 13, wherein the electrogram comprises an atrial electrocardiogram, and identifying features further comprises:
identifying a first feature in the atrial electrocardiogram as an indication of primary near field depolarization when the first feature appears in the fine and coarse scale wavelets;
identifying a second feature in the atrial electrocardiogram as a secondary near field depolarization when the second feature appears in the fine scales wavelets but not the coarse scale wavelets; and
identifying a third feature in the atrial electrocardiogram as a far field primary depolarization when the third feature appears in the coarse scale wave lets but not the tine scale wavelets.

19. A computer readable medium comprising computer readable instructions that when executed:
convert an electrogram into a set of wavelets, the set of wavelets including wavelets at a fine scale and wavelets at a coarse scale; and
identify features of the electrogram based on whether the features appear in only the fine scale wavelets, only the coarse scale wavelets or both the fine and coarse scale wavelets.

20. The computer readable medium of claim 19, wherein wavelets in the coarse scale have a scale factor greater than or equal to 10 multiplied by a scale factor associated with wavelets in the fine scale.

21. The computer readable medium of claim 19, further comprising computer readable instructions that when executed identify a particular feature in the electrogram as a large amplitude steep deflection when the particular feature appears in the fine and coarse scale wavelets.

22. The computer readable medium of claim 19, further comprising computer readable instructions that when executed identify a particular feature in the electrogram as a small amplitude steep deflection when the particular feature appears in the fine scales wavelets but not the coarse scale wavelets.

23. The computer readable medium of claim 19, further comprising computer readable instructions that when executed identify a particular feature in the electrogram as a large amplitude shallow deflection when the particular feature appears in the coarse scale wavelets but not the fine scale wavelets.

24. The computer readable medium of claim 19, wherein the electrogram comprises an atrial electrocardiogram, further comprising computer readable instructions that when executed:
identify a first feature in the atrial electrocardiogram as an indication of primary near field depolarization when the first feature appears in the fine and coarse scale wavelets;
identify a second feature in the atrial electrocardiogram as a secondary near field depolarization when the second feature appears in the fine scales wavelets but not the coarse scale wavelets; and
identify a third feature in the atrial electrocardiogram as a far field primary depolarization when the third feature appears in the coarse scale wavelets but not the fine scale wavelets.

25. An apparatus comprising:
means for converting an electrogram into a set of wavelets, the set of wavelets including wavelets at a fine scale and wavelets at a coarse scale; and
means for identifying features of the electrogram based on whether the features appear in only the fine scale wavelets, only the coarse scale wavelets or both the fine and coarse scale wavelets.

26. The apparatus of claim 25, further comprising means for identifying a particular feature in the electrogram as a large amplitude steep deflection when the particular feature appears in the fine and coarse scale wavelets.

27. The apparatus of claim 25, further comprising means for identifying a particular feature in the electrogram as a small amplitude steep deflection when the particular feature appears in the fine scales wavelets but not the coarse scale wavelets.

28. The apparatus of claim 25, further comprising means for identifying a particular feature in the electrogram as a large amplitude shallow deflection when the particular feature appears in the coarse scale wavelets but not the fine scale wavelets.

29. A method comprising:
converting an biomedical signal into a set of wavelets, the set of wavelets including wavelets at a fine scale and wavelets at a coarse scale; and
identifying features of the biomedical signal based on whether the features appear in only the fine scale wavelets, only the coarse scale wavelets or both the fine and coarse scale wavelets.

30. The method of claim 29, wherein the biomedical signal comprises a signal selected from the group consisting of: an electrogram measured via external sensors, an electrogram measured via implanted sensors, and a signal measured by a biomedical sensor.

* * * * *

UNITED STATES PATENT AND TRADEMARK OFFICE
CERTIFICATE OF CORRECTION

PATENT NO. : 7,082,327 B2
APPLICATION NO. : 10/414758
DATED : July 25, 2006
INVENTOR(S) : Houben

Page 1 of 1

It is certified that error appears in the above-identified patent and that said Letters Patent is hereby corrected as shown below:

Column 13, line 52, change "tine" to --fine--.

Signed and Sealed this

Twenty-sixth Day of December, 2006

JON W. DUDAS
*Director of the United States Patent and Trademark Office*